(12) United States Patent
Tropmann et al.

(10) Patent No.: US 8,939,763 B2
(45) Date of Patent: Jan. 27, 2015

(54) DENTAL IMPRESSION TRAY WITH ABSORBENT BARRIERS

(75) Inventors: Aaron Tropmann, Wake Forest, NC (US); Ricky D. Robinson, Zebulon, NC (US); Lawrence William Mckee II, Apex, NC (US)

(73) Assignee: Blue Water Dental Innovations, LLC, Wake Forest, NC (US)

( * ) Notice: Subject to any disclaimer, the term of this patent is extended or adjusted under 35 U.S.C. 154(b) by 0 days.

(21) Appl. No.: 13/033,754

(22) Filed: Feb. 24, 2011

(65) Prior Publication Data

US 2012/0219925 A1 Aug. 30, 2012

(51) Int. Cl.
*A61C 9/00* (2006.01)

(52) U.S. Cl.
USPC .......................................................... 433/37

(58) Field of Classification Search
CPC ......... A61C 13/30; A61C 9/00; A61C 9/0006
USPC ....................... 433/34, 36, 37, 38, 48, 68–71, 433/136–138, 214; 128/848, 861, 862
See application file for complete search history.

(56) References Cited

U.S. PATENT DOCUMENTS

| | | | | |
|---|---|---|---|---|
| 1,234,958 A | * | 7/1917 | Supplee et al. | 433/48 |
| 1,517,197 A | * | 11/1924 | Vincent | 433/48 |
| 1,778,293 A | * | 10/1930 | Galasso | 433/37 |
| 1,979,493 A | * | 11/1934 | Salvio | 433/38 |
| 2,011,860 A | * | 8/1935 | Louis | 433/48 |
| 2,043,294 A | * | 6/1936 | Louis | 433/47 |
| 2,183,624 A | * | 12/1939 | Schwartz et al. | 433/71 |
| 2,598,927 A | * | 6/1952 | May | 433/47 |
| 2,634,500 A | * | 4/1953 | McAdoo | 433/38 |
| 3,064,354 A | * | 11/1962 | Pos | 433/71 |
| 3,468,029 A | * | 9/1969 | Moore | 433/38 |
| 3,501,837 A | * | 3/1970 | Clark | 433/38 |
| 4,204,323 A | * | 5/1980 | Neubert et al. | 433/38 |
| D266,269 S | * | 9/1982 | Werrin | D24/181 |
| 4,449,927 A | * | 5/1984 | Taylor et al. | 433/38 |
| 4,472,140 A | * | 9/1984 | Lustig | 433/38 |
| 4,530,662 A | * | 7/1985 | Andersson et al. | 433/37 |
| 4,531,914 A | * | 7/1985 | Spinello | 433/136 |
| 4,619,610 A | * | 10/1986 | Pelerin | 433/41 |
| 4,689,010 A | * | 8/1987 | Wolfe | 433/38 |
| 4,867,680 A | * | 9/1989 | Hare et al. | 433/37 |

(Continued)

*Primary Examiner* — Heidi M Eide
*Assistant Examiner* — Matthew Saunders
(74) *Attorney, Agent, or Firm* — Ash Tankha; Robert James Yarbrough; Lipton, Weinberger & Husick

(57) ABSTRACT

A dental impression apparatus for obtaining a patient's dental impression is provided. The dental impression apparatus includes a support frame of a predefined shape, a partially permeable membrane mounted on the support frame, and absorbent barrier members. The support frame includes a distal member, a buccal edge member, and a lingual edge member. The absorbent barrier members mounted to the buccal edge member and the lingual edge member of the support frame define opposing troughs separated by the partially permeable membrane. The opposing troughs receive the patient's mandibular teeth and maxillary teeth. The opposing troughs are deposited with a first impression material and/or a second impression material for obtaining the dental impression of the patient. The absorbent barrier members confine a flow of the first impression material and the second impression material within the opposing troughs, when the patient applies a biting force within the opposing troughs.

4 Claims, 14 Drawing Sheets

(56) References Cited

U.S. PATENT DOCUMENTS

| | | | | |
|---|---|---|---|---|
| 4,978,298 A * | 12/1990 | Eliasz | | 433/213 |
| 4,995,540 A * | 2/1991 | Colin et al. | | 222/132 |
| 5,011,407 A * | 4/1991 | Pelerin | | 433/48 |
| 5,190,457 A * | 3/1993 | Schreinemakers | | 433/214 |
| 5,266,031 A * | 11/1993 | Marigza | | 433/71 |
| 5,297,960 A * | 3/1994 | Burns | | 433/41 |
| 5,370,533 A * | 12/1994 | Bushnell | | 433/36 |
| 5,503,552 A * | 4/1996 | Diesso | | 433/37 |
| 5,582,517 A * | 12/1996 | Adell | | 433/6 |
| 5,636,985 A * | 6/1997 | Simmen et al. | | 433/37 |
| 5,676,543 A * | 10/1997 | Dragan | | 433/136 |
| 5,718,577 A * | 2/1998 | Oxman et al. | | 433/37 |
| 5,718,586 A * | 2/1998 | Sharp et al. | | 433/214 |
| 5,722,832 A * | 3/1998 | White | | 433/214 |
| 5,733,118 A * | 3/1998 | Pankuch et al. | | 433/38 |
| 5,807,100 A * | 9/1998 | Thornton | | 433/48 |
| 5,820,372 A * | 10/1998 | Jones | | 433/38 |
| 5,846,082 A * | 12/1998 | Thornton | | 433/215 |
| 6,017,217 A * | 1/2000 | Wittrock | | 433/37 |
| 6,116,905 A * | 9/2000 | Hoos | | 433/214 |
| 6,201,038 B1 | 3/2001 | Waller et al. | | 523/109 |
| 6,247,926 B1 * | 6/2001 | Thornton | | 433/48 |
| 6,379,147 B1 * | 4/2002 | Georgakis et al. | | 433/37 |
| 6,450,808 B1 * | 9/2002 | Pelerin | | 433/38 |
| D464,138 S * | 10/2002 | Werrin | | D24/181 |
| 6,561,807 B2 * | 5/2003 | Hare | | 433/214 |
| 6,726,477 B2 * | 4/2004 | Gittleman | | 433/34 |
| 6,817,861 B1 * | 11/2004 | Roetzer | | 433/37 |
| 6,835,065 B1 * | 12/2004 | Wise | | 433/38 |
| 6,843,652 B2 * | 1/2005 | Xie et al. | | 433/90 |
| 6,902,398 B1 * | 6/2005 | Segal | | 433/38 |
| 6,913,461 B2 * | 7/2005 | Gittleman | | 433/38 |
| 7,021,929 B2 * | 4/2006 | DiMarino et al. | | 433/38 |
| 7,101,179 B2 * | 9/2006 | Liddle | | 433/38 |
| 7,137,813 B1 * | 11/2006 | Roetzer | | 433/37 |
| 7,220,123 B1 * | 5/2007 | Karapetyan | | 433/37 |
| 7,234,933 B2 * | 6/2007 | Bergersen | | 433/6 |
| 7,270,540 B2 * | 9/2007 | Skinner | | 433/43 |
| 2002/0064753 A1 * | 5/2002 | Philp, Jr. | | 433/32 |
| 2003/0044748 A1 * | 3/2003 | Tucker et al. | | 433/38 |
| 2003/0138754 A1 * | 7/2003 | DiMarino et al. | | 433/37 |
| 2003/0180680 A1 * | 9/2003 | Burgio et al. | | 433/37 |
| 2003/0224319 A1 * | 12/2003 | Liddle | | 433/38 |
| 2004/0023185 A1 * | 2/2004 | Gittleman | | 433/34 |
| 2004/0043353 A1 * | 3/2004 | Detje | | 433/37 |
| 2004/0096800 A1 * | 5/2004 | Tucker et al. | | 433/38 |
| 2004/0096801 A1 * | 5/2004 | Tucker et al. | | 433/38 |
| 2004/0096802 A1 * | 5/2004 | Gittleman | | 433/71 |
| 2004/0101803 A1 * | 5/2004 | Tucker et al. | | 433/38 |
| 2004/0110112 A1 * | 6/2004 | Xie et al. | | 433/89 |
| 2004/0219475 A1 * | 11/2004 | DiMarino et al. | | 433/38 |
| 2005/0095553 A1 * | 5/2005 | Gittleman | | 433/37 |
| 2006/0172253 A1 * | 8/2006 | Pumphrey et al. | | 433/37 |
| 2006/0269904 A1 * | 11/2006 | Suchan et al. | | 433/213 |
| 2007/0037116 A1 * | 2/2007 | Knutson | | 433/68 |
| 2007/0054237 A1 * | 3/2007 | Neuschafer | | 433/37 |
| 2007/0259313 A1 * | 11/2007 | Dragan et al. | | 433/136 |
| 2008/0096158 A1 * | 4/2008 | Dorfman et al. | | 433/37 |
| 2008/0280249 A1 * | 11/2008 | Choi | | 433/38 |

* cited by examiner

DENTAL IMPRESSION TRAY WITH ABSORBENT BARRIERS

BACKGROUND

To fabricate a dental prosthesis for a patient, a dental impression of a dentition of the patient is required. At present, a sequence of steps is followed to obtain the dental impression. The impression of prepared teeth such as maxillary teeth or mandibular teeth of a desired dental arch is obtained. The impression of the opposing dental arch is then obtained. A bite registration is then fabricated to interdigitate each impression to enable a dental practitioner to fabricate the dental prosthesis. During this procedure, a dental practitioner must perform retraction of free tissues such as tongue, cheek, lips, etc., retraction of attached tissues such as gingival margins around an individual tooth, control of moisture, saliva, blood, etc., and monitor the patient to prevent gagging. Performing each of these functions sequentially is time consuming and difficult.

Although, current impression devices allow a dental practitioner to capture both the dental arches at once, these devices lack techniques or construction to manage the free tissues, the attached tissues, and/or the moisture contaminants of an oral cavity. Current practices involve auxiliary steps for the management of tissues, for example, mechanical retraction, altered tissue dynamics using laser, electrosurge, etc., or chemical alteration. Hence, there is a need for an apparatus that expedites the procedure for obtaining a dental impression by minimizing the sequence of steps currently followed. There is also a need for an apparatus that effectively employs dental impression materials around the teeth of interest for obtaining an accurate dental impression of the patient.

Therefore, there is a long felt but unresolved need for a dental impression apparatus that accurately obtains a dental impression of a patient with a minimum number of steps. Furthermore, there is a need for a dental impression apparatus that effectively employs the dental impression materials to accurately obtain the dental impression of the patient, while preventing contamination of the dental impression by moisture, saliva, blood, etc.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The dental impression apparatus and method disclosed herein address the above stated needs for accurately obtaining a dental impression of a patient with a minimum number of steps by effectively employing dental impression materials around teeth of interest, while preventing contamination of the dental impression by moisture, saliva, blood, etc.

The dental impression apparatus disclosed herein comprises a support frame of a predefined shape, a partially permeable membrane, and absorbent barrier members. The support frame comprises a distal member, a buccal edge member and a lingual edge member extending from the opposing ends of the distal member. The buccal edge member and the lingual edge member of the support frame are attached to the opposing ends of the distal member of the support frame. In an embodiment, the predefined shape of the support frame conforms to a dental arch of one or more molar and premolar regions of the mandibular teeth and the maxillary teeth of the patient. The distal member of the support frame is positioned around one of the posterior molar teeth of the patient when obtaining the dental impression of the patient. The partially permeable membrane is mounted between the buccal edge member and the lingual edge member of the support frame.

The pair of absorbent barrier members is mounted onto each of the buccal edge member and the lingual edge member of the support frame. The absorbent barrier members mounted to the buccal edge member and the lingual edge member define opposing troughs separated by the partially permeable membrane. As used herein, each of the troughs refers to a channel of space defined by the partially permeable membrane and the upper absorbent barrier members mounted on the buccal edge member and the lingual edge member or the lower absorbent barrier members mounted on the buccal edge member and the lingual edge member. The opposing troughs are configured to receive mandibular teeth and maxillary teeth of the patient. The dental impression apparatus further comprises a handle attached to and extending outwardly from the buccal edge member of the support frame for holding the dental impression apparatus.

The opposing troughs defined by the dental impression apparatus disclosed herein are deposited with one or more of a first impression material and a second impression material for obtaining the dental impression of the patient. The first impression material is, for example, of a substantially higher viscosity than the second impression material. The first impression material of a substantially higher viscosity than the second impression material forces the second impression material within interstitial spaces of the maxillary teeth and the mandibular teeth. The absorbent barrier members confine a flow of the first impression material and the second impression material within the opposing troughs of the dental impression apparatus, when the patient applies a biting force within the opposing troughs. Furthermore, the absorbent barrier members absorb moisture, saliva, blood, etc., within the patient's oral cavity and prevent contamination of the dental impression during the procedure. The dental impression of each of the mandibular teeth and the maxillary teeth is obtained on the second impression material and the first impression material. The dental impression apparatus and method disclosed herein reduces chair time, is more comfortable for the patient, and allows capture of a more accurate centric occlusion of the patient.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1A:
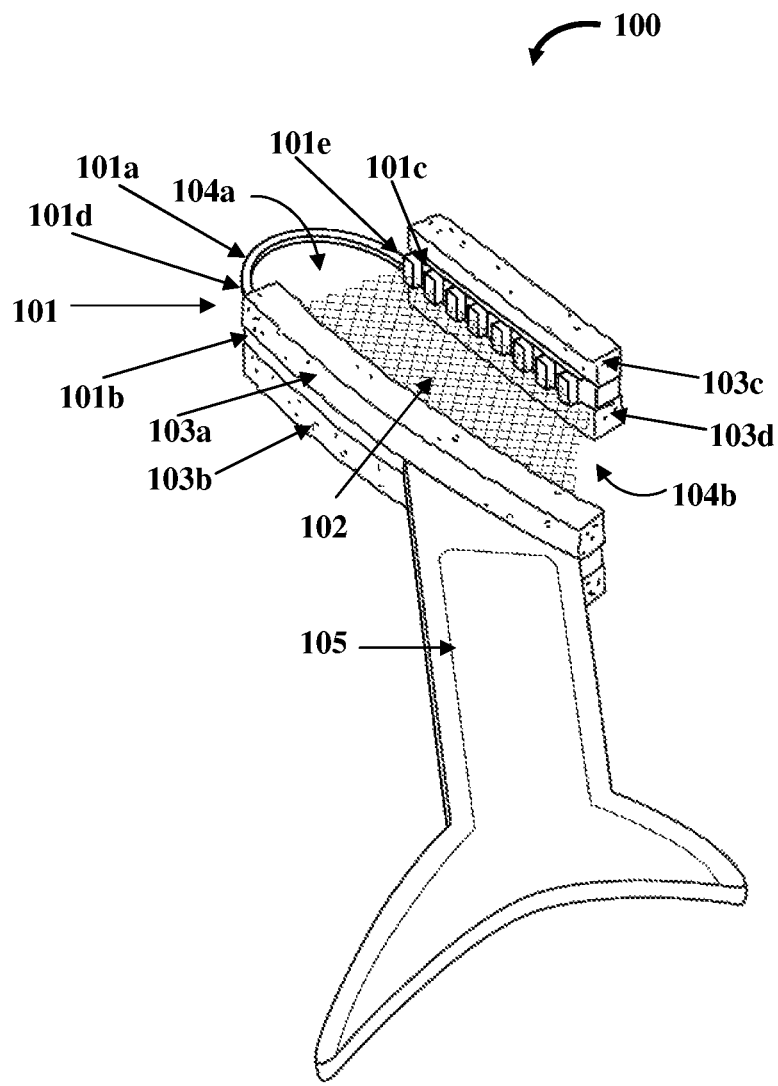
FIG. 1A exemplarily illustrates a perspective view of a dental impression apparatus.
Figure 1B:
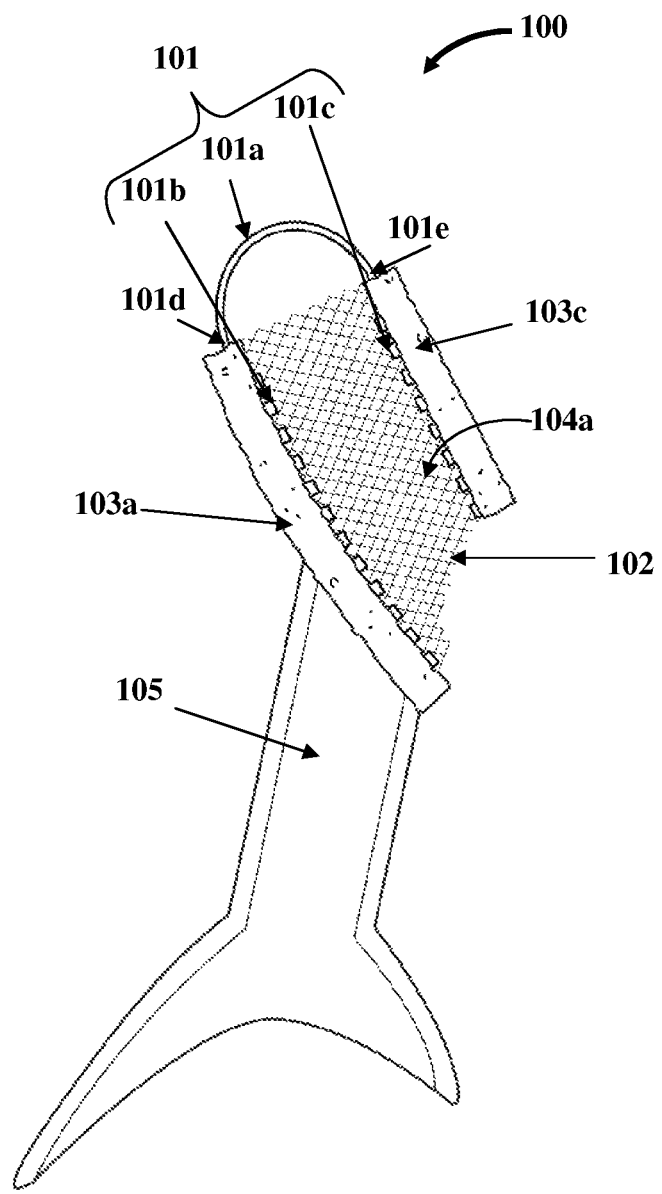
FIG. 1B exemplarily illustrates a top orthogonal view of the dental impression apparatus.

FIG. 1A and FIG. 1B exemplarily illustrate a perspective and a top orthogonal view of a dental impression apparatus 100 respectively, for obtaining a dental impression of a patient. The term "dental impression" refers to an accurate representation of a part or all of a patient's dentition comprising, for example, maxillary teeth 305b and mandibular teeth 305a as exemplarily illustrated in FIG. 5. The dental impression apparatus 100 disclosed herein comprises a support frame 101, a partially permeable membrane 102, absorbent barrier members 103a, 103b and 103c, 103d mounted on the support frame 101, and a handle 105. The support frame 101 is of a predefined shape as disclosed in the detailed description of FIGS. 4-5. The support frame 101 comprises a distal member 101a, a buccal edge member 101b and a lingual edge member 101c extending from the distal member 101a. The distal member 101a of the support frame 101 is substantially semi-circular is shape.

The buccal edge member 101b and the lingual edge member 101c of the support frame 101 extend from and are attached to the opposing ends 101d and 101e of the distal member 101a of the support frame 101. As used herein, the buccal edge member 101b refers to a lateral edge of the dental impression apparatus 100 that is disposed proximal to a cheek of the patient. As used herein, the lingual edge member 101c refers to a lateral edge of the dental impression apparatus 100 that is disposed proximal to the tongue of the patient. Materials used for constructing the support frame 101 comprise, for example, one or more of metal alloys, stainless steel, high density polyethylene, etc.

The partially permeable membrane 102 is, for example, a mesh that allows limited passage of one or more substances, for example, dental impression materials 301 and 303, contaminants, etc. As exemplarily illustrated in FIG. 1A, the partially permeable membrane 102 is mounted between the buccal edge member 101b and the lingual edge member 101c of the support frame 101. The partially permeable membrane 102 is made from materials such as cotton fabric, a nylon mesh, a polyethylene screen, etc. The absorbent barrier members 103a, 103b and 103c, 103d mounted to the buccal edge member 101b and the lingual edge member 101c of the support frame 101 respectively are disclosed in the detailed description of FIG. 2. The absorbent barrier members 103a, 103b and 103c, 103d are of a uniform height and about the length of an exposed portion of the mandibular teeth 305a and maxillary teeth 305b surface over an entire length of said absorbent barrier members.

The handle 105 of the dental impression apparatus 100 is attached to the buccal edge member 101b of the support frame 101 for holding the dental impression apparatus 100. The handle 105 extends outwardly from the buccal edge member 101b of the support frame 101. The handle 105 is shaped to resemble, for example, a sword fish tail as exemplarily illustrated in FIGS. 1A-1B, FIGS. 3A-3B, and FIGS. 4-5. The handle 105 is made from materials comprising, for example, one or more of metal alloys, stainless steel, high density polyethylene, etc.

Figure 2:
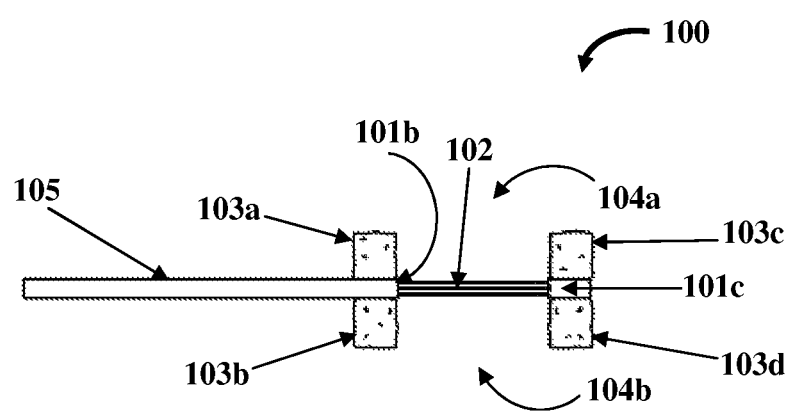
FIG. 2 exemplarily illustrates a front orthogonal view of the dental impression apparatus.

FIG. 2 exemplarily illustrates a front orthogonal view of the dental impression apparatus 100. A pair of absorbent barrier members 103a, 103b and 103c, 103d of the dental impression apparatus 100 is mounted onto the buccal edge member 101b and the lingual edge member 101c of the support frame 101 respectively. The absorbent barrier members 103a, 103b and 103c, 103d mounted to the buccal edge member 101b and the lingual edge member 101c define opposing troughs 104a and 104b separated by the partially permeable membrane 102 of the dental impression apparatus 100. The opposing troughs 104a and 104b comprise an upper trough 104a and a lower trough 104b. As used herein, the upper trough 104a refers to a channel of space defined by the partially permeable membrane 102 and the absorbent barrier members 103a and 103c mounted on the buccal edge member 101b and the lingual edge member 101c respectively. Also, as used herein, the lower trough 104b refers to a channel of space defined by the partially permeable membrane 102 and the absorbent barrier members 103b and 103d mounted on the buccal edge member 101b and the lingual edge member 101c respectively.

The opposing troughs 104a and 104b, that is the upper trough 104a above the partially permeable membrane 102 and the lower trough 104b below the partially permeable membrane 102, are configured to receive maxillary teeth 305b and mandibular teeth 305a of the patient respectively as exemplarily illustrated in FIGS. 4-5 and FIGS. 8A-8F. The maxillary teeth 305b refer to the upper teeth in the upper jaw or maxilla of the patient. The mandibular teeth 305a refer to the lower teeth in the lower jaw or mandible of the patient. In an embodiment, the absorbent barrier members 103a, 103b and 103c, 103d are mounted along a length of the buccal edge member 101b and the lingual edge member 101c respectively. The absorbent barrier members 103a, 103b and 103c, 103d absorb moisture, saliva, blood, etc., within the patient's oral cavity and prevent contamination of a dental impression obtained by the dental impression apparatus 100. The absorbent barrier members 103a, 103b and 103c, 103d are made from materials comprising, for example, one or more of low density polyethylene foam, a cotton sponge, a cotton polyethylene blend, etc. Hence, the absorbent barrier members 103a, 103b, 103c and 103d are soft and configured for comfort to the patient using the dental impression apparatus.

Figure 3A:
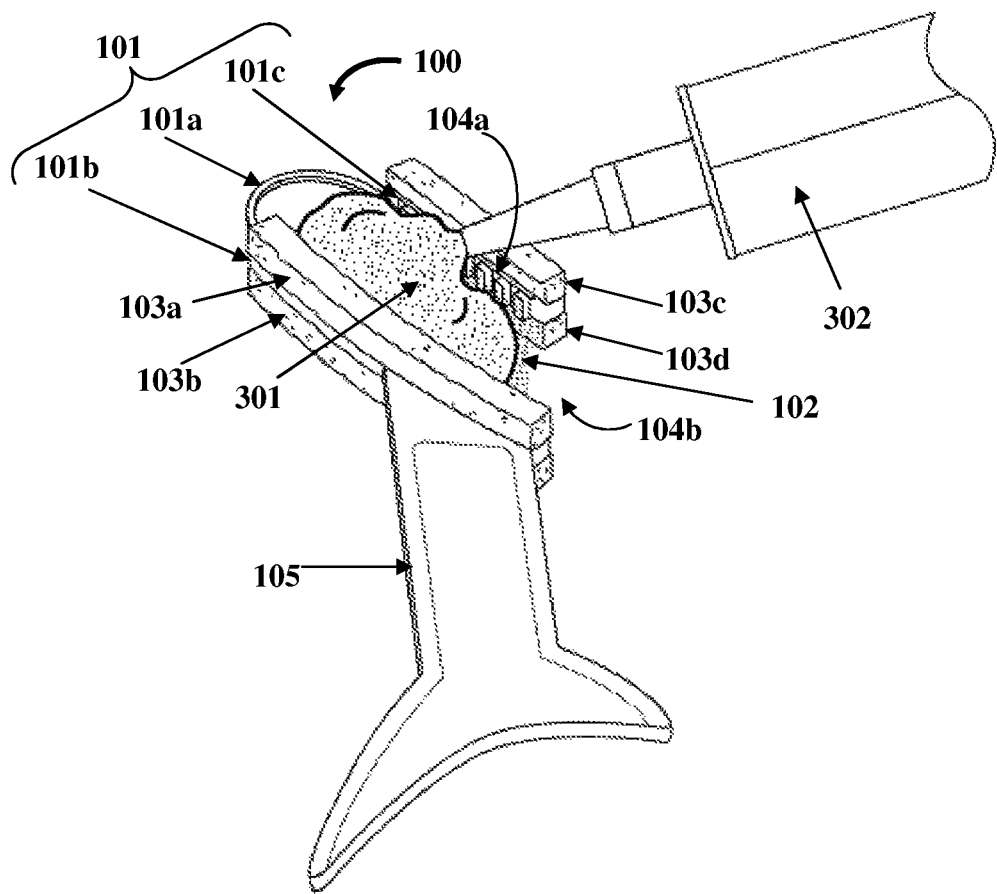
FIG. 3A exemplarily illustrates a perspective view of the dental impression apparatus, showing application of a first impression material having a high viscosity on an upper trough of the dental impression apparatus.
Figure 3B:
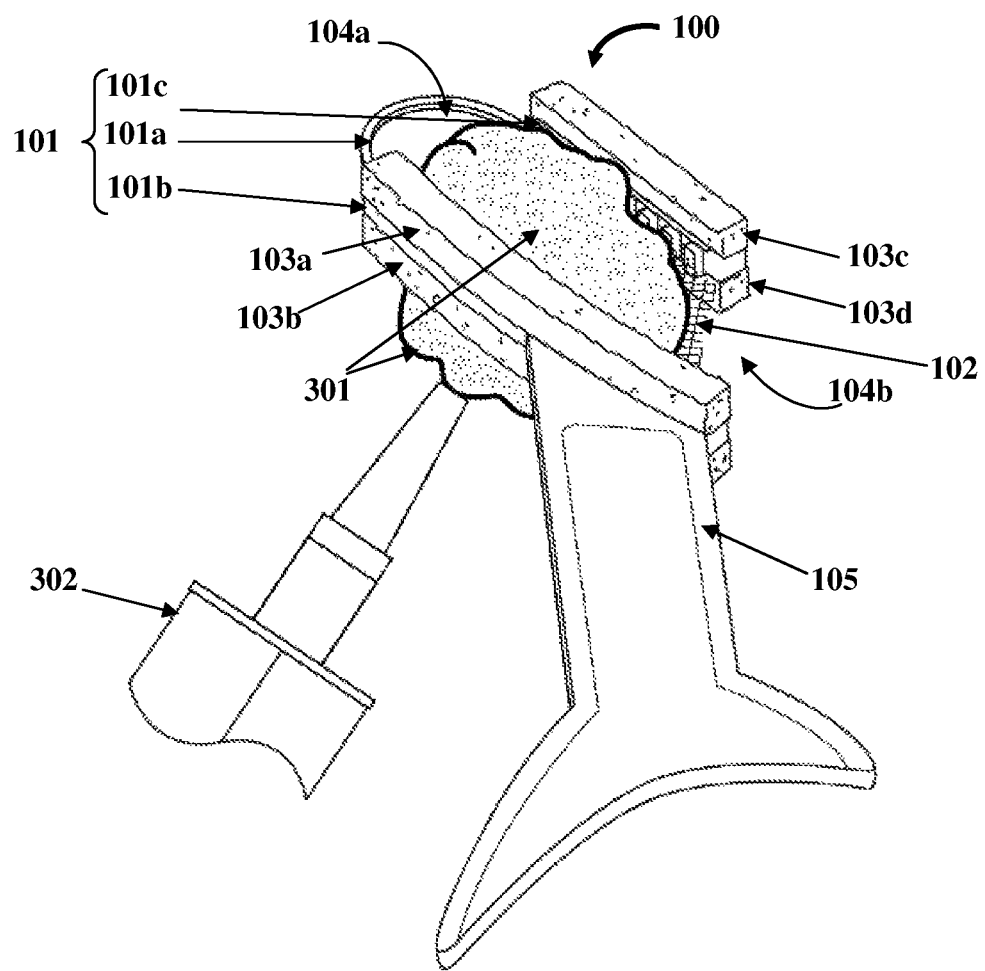
FIG. 3B exemplarily illustrates a perspective view of the dental impression apparatus, showing application of a first impression material having a high viscosity on a lower trough of the dental impression apparatus.
Figure 4:
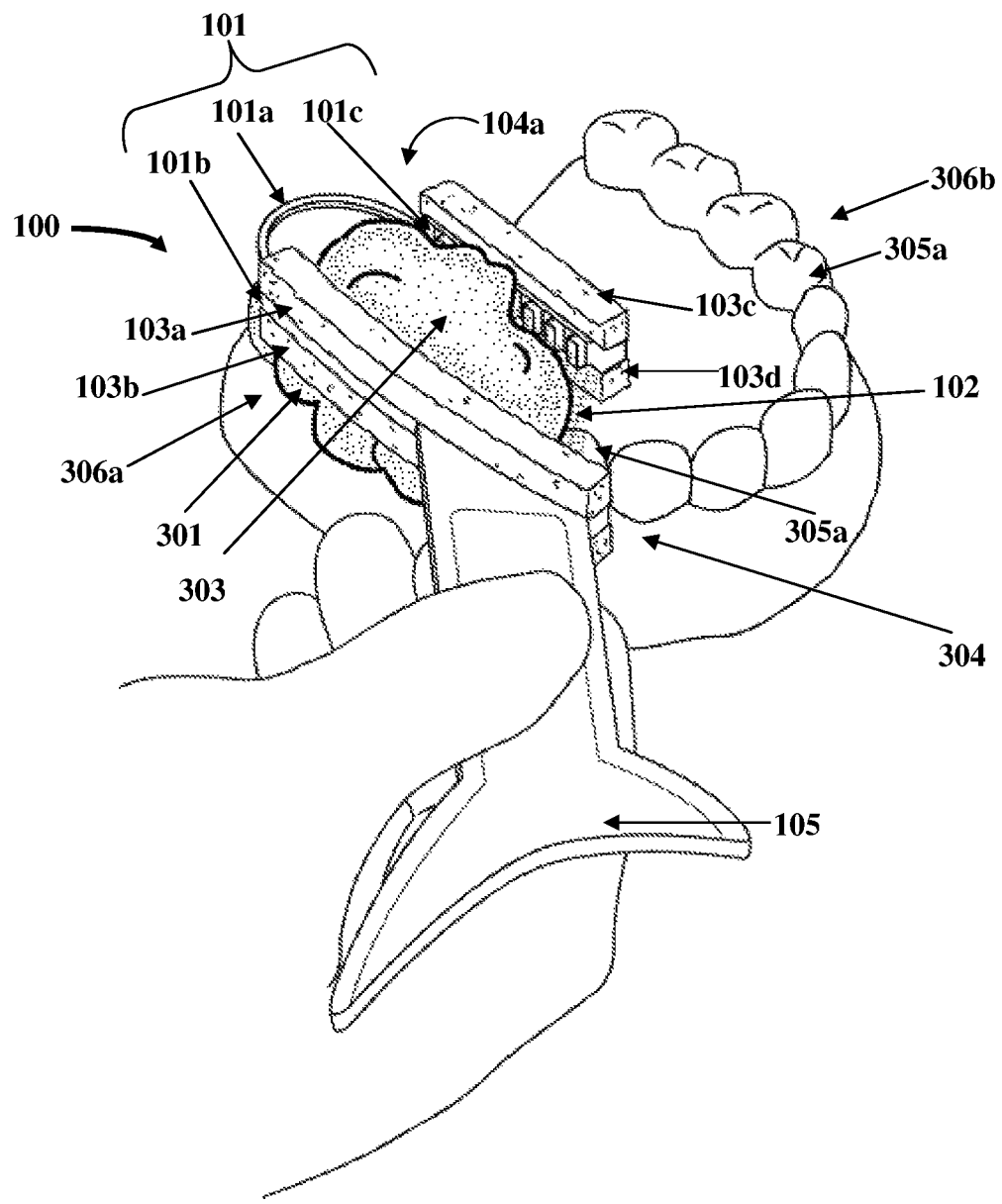
FIG. 4 exemplarily illustrates a perspective view of the dental impression apparatus for obtaining a dental impression of mandibular teeth of the patient.
Figure 5:
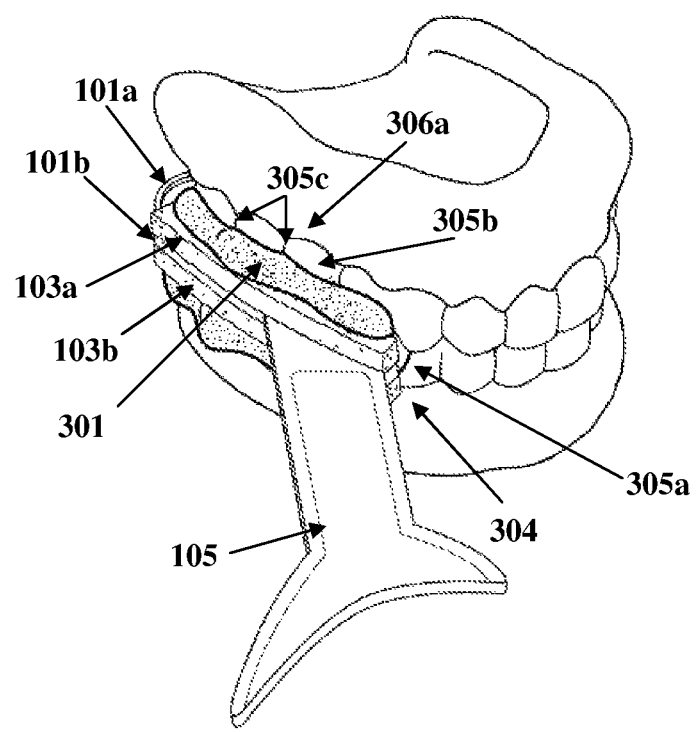
FIG. 5 exemplarily illustrates a perspective view of the dental impression apparatus for obtaining a dental impression of the mandibular teeth and maxillary teeth of the patient.

The opposing troughs 104a and 104b are configured to receive the mandibular teeth 305a as disclosed in the detailed description of FIG. 4 and the maxillary teeth 305b as disclosed in the detailed description of FIG. 5. The opposing troughs 104a and 104b are deposited with a first impression material 301 and/or a second impression material 303, as exemplarily illustrated in FIGS. 3A-3B and FIG. 4, for obtaining the dental impression of the patient as disclosed in the detailed description of FIGS. 4-5. The absorbent barrier members 103a, 103b and 103c, 103d confine a flow of the first impression material 301 and the second impression material 303 within the opposing troughs 104a and 104b, when the patient applies a biting force within the opposing troughs 104a and 104b as exemplarily illustrated in FIG. 5.

FIG. 3A and FIG. 3B exemplarily illustrate perspective views of the dental impression apparatus 100, showing application of the first dental impression material 301 having a high viscosity on an upper trough 104a and a lower trough 104b of the dental impression apparatus 100 respectively. The dental impression apparatus 100 disclosed herein comprises the support frame 101 having the distal member 101a, the buccal edge member 101b and the lingual edge member 101c, the partially permeable membrane 102, the absorbent barrier members 103a, 103b and 103c, 103d, and the handle 105 as disclosed in the detailed description of FIGS. 1A-1B and FIG. 2. The first dental impression material 301 having a high viscosity is applied to the upper trough 104a defined by the partially permeable membrane 102 and the absorbent barrier members 103a and 103c mounted on the buccal edge member 101b and the lingual edge member 101c respectively as exemplarily illustrated in FIG. 3A. The first dental impression material 301 having a high viscosity is also applied to the lower trough 104b defined by the partially permeable membrane 102 and the absorbent barrier members 103b and 103d mounted on the buccal edge member 101b and the lingual edge member 101c respectively as exemplarily illustrated in FIG. 3B. A dispensing tube 302 containing the first dental impression material 301 is used for dispensing the first dental impression material 301, having a high viscosity, onto the troughs 104a and 104b defined by the dental impression apparatus 100. A dispensing tube 307 containing the second dental impression material 303 is used for dispensing the second dental impression material 303, having a low viscosity, as a thin layer on top of the first dental impression material 301.

Figure 3C:
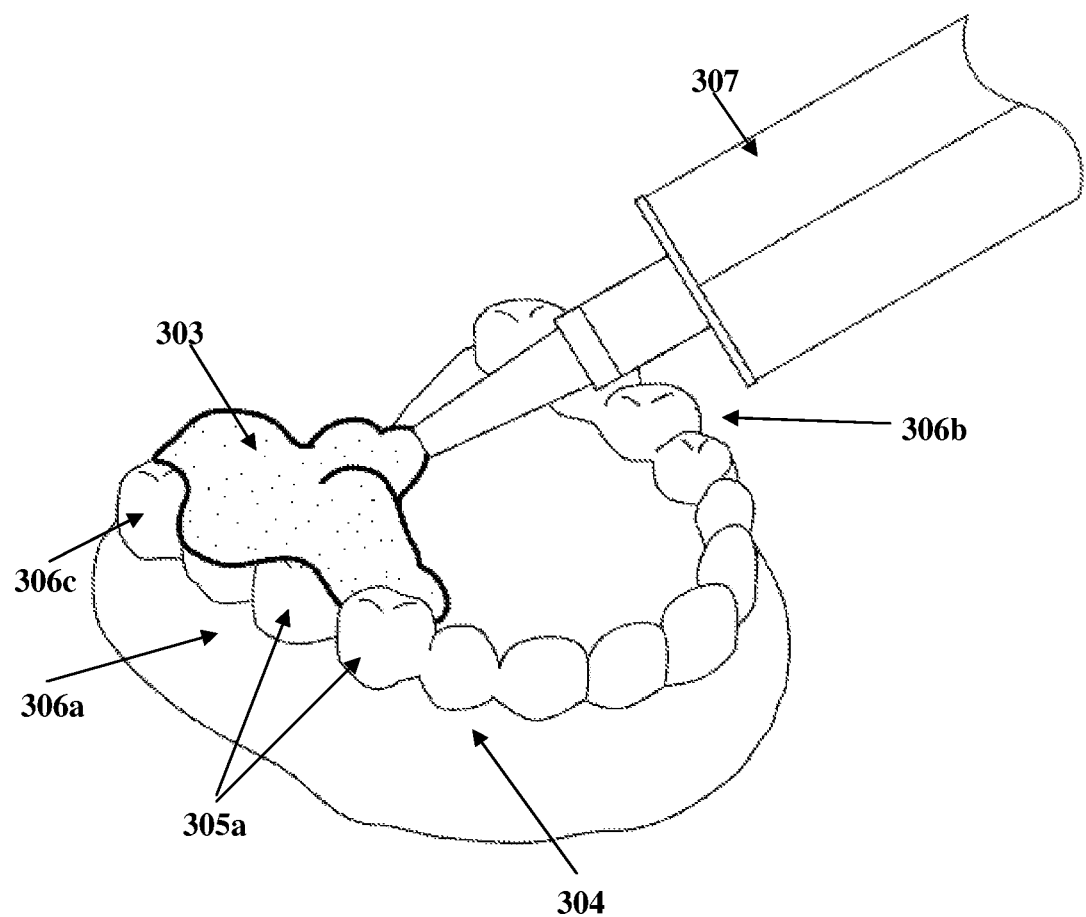
FIG. 3C exemplarily illustrates application of a second impression material having a low viscosity to mandibular teeth of a patient.

FIG. 3C exemplarily illustrates application of a second dental impression material 303 onto the mandibular teeth 305a of a patient. The second dental impression material 303 has a viscosity substantially lower than the viscosity of the first dental impression material 301 exemplarily illustrated in FIGS. 3A-3B. The first dental impression material 301 is of a substantially higher viscosity than the second dental impression material 303. FIG. 3C also illustrates a dental arch 304, and one or more molar and premolar regions 306a and 306b of the mandibular teeth 305a. A second dispensing tube 307 containing the second dental impression material 303 is used for dispensing and depositing the second dental impression material 303 having a low viscosity at ambient temperature onto the mandibular teeth 305a of the patient.

In an embodiment, the first impression material 301 shown by dense shading in FIGS. 3A-3B and the second impression material 303 shown by sparse shading in FIG. 3C are both deposited in the troughs 104a and 104b as exemplarily illustrated in FIG. 4. The second impression material 303 is applied as a thin layer over the first impression material 301 in the troughs 104a and 104b. The first impression material 301 and the second impression material 303 comprise, for example, polymers of different viscosities selected based on curing characteristics required for the dental impression or according to needs or preferences of a dental practitioner. Examples of the first impression material 301 and the second impression material 303 comprise vinyl polysiloxanes (VPS), polyethers, hydrocolloids, etc. The first impression material 301 having a high viscosity confines and drives the second impression material 303 having a low viscosity deeper and tighter around the maxillary teeth 305b and the mandibular teeth 305a of the patient.

FIG. 4 exemplarily illustrates a perspective view of the dental impression apparatus 100 for obtaining a dental impression of the mandibular teeth 305a of the patient. The dental impression apparatus 100 comprises the support frame 101, the partially permeable membrane 102, and the absorbent barrier members 103a, 103b and 103c, 103d as disclosed in the detailed description of FIGS. 1A-1B and FIG. 2. In an embodiment, the predefined shape of the support frame 101 conforms to a dental arch 304 of one or more molar regions 306a and 306b of the mandibular teeth 305a and the maxillary teeth 305b of the patient. In another embodiment, the predefined shape of the support frame 101 conforms to a dental arch 304 of one or more molar and premolar regions 306a and 306b of the mandibular teeth 305a and the maxillary teeth 305b of the patient. The dental impression apparatus 100 with the deposited first impression material 301 and second impression material 303 in the troughs 104a and 104b is positioned in the patient's mouth to receive the maxillary teeth 305b and the mandibular teeth 305a. The distal member 101a of the support frame 101 is positioned around one of the patient's posterior molar teeth 306c, when obtaining the dental impression of the patient.

FIG. 5 exemplarily illustrates a perspective view of the dental impression apparatus 100 for obtaining a dental impression of the mandibular teeth 305a and the maxillary teeth 305b of the patient. The dental impression apparatus 100 comprising the support frame 101, the partially permeable membrane 102, the absorbent barrier members 103a, 103b and 103c, 103d, and the handle 105 as disclosed in the detailed description of FIGS. 1A-1B and FIG. 2 is inserted in the patient's mouth to receive the maxillary teeth 305b and the mandibular teeth 305a. The support frame 101 is of a predefined shape that conforms to the dental arch 304 of one or more molar and premolar regions 306a and 306b of the mandibular teeth 305a and the maxillary teeth 305b of the patient. FIG. 5 exemplarily illustrates the confinement of the first impression material 301 within the opposing troughs 104a and 104b by the absorbent barrier members 103a, 103b and 103c, 103d, when the patient applies a biting force within the opposing troughs 104a and 104b exemplarily illustrated in FIG. 2.

The first impression material 301 deposited in the opposing troughs 104a and 104b is of a substantially higher viscosity than the second impression material 303 deposited on the first impression material 301 in the opposing troughs 104a and 104b. The absorbent barrier members 103a, 103b and 103c, 103d attached to the buccal edge member 101b and the lingual edge member 101c of the support frame 101 respectively restrict lateral expansion of the first impression material 301 having a high viscosity. The restriction of the lateral expansion of the first impression material 301 having a high viscosity drives the second impression material 303 having a low viscosity deeper into and tighter around the mandibular teeth 305a and the maxillary teeth 305b, thereby creating an accurate dental impression of the patient on the first impression material 301 and the second impression material 303. When the lateral expansion of the first impression material 301 is restricted, the first impression material 301 forces the second impression material 303 deeper into the interstitial spaces 305c of the maxillary teeth 305b and the mandibular teeth 305a to obtain high precision dental impressions 601a and 601b respectively as exemplarily illustrated in FIGS. 6A-6B. With pressure dynamics exhibited by the lateral absorbent barrier members 103a, 103b and 103c, 103d, the need for mechanical retraction, altered tissue dynamics, or chemical alteration is substantially reduced or eliminated.

Figure 6A:
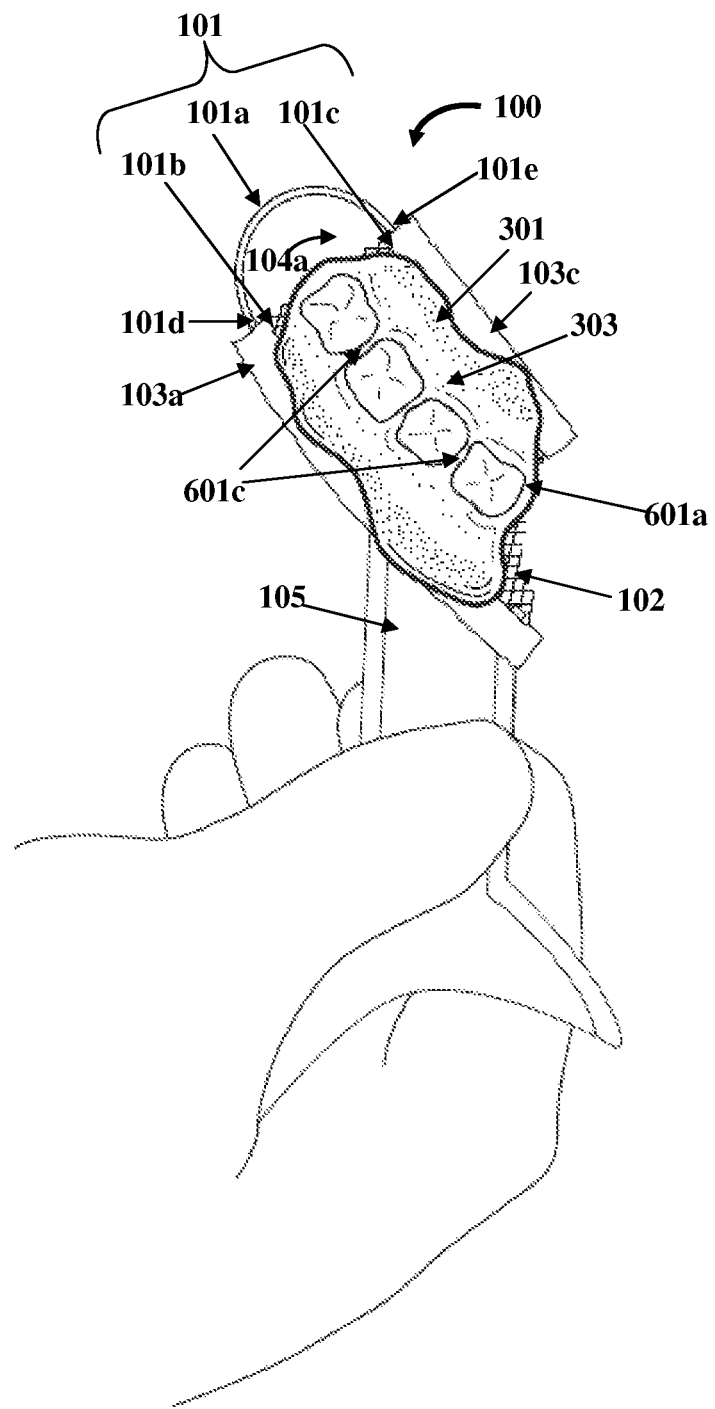
FIG. 6A exemplarily illustrates an orthogonal view of the dental impression apparatus, showing a dental impression of the maxillary teeth of the patient.
Figure 6B:
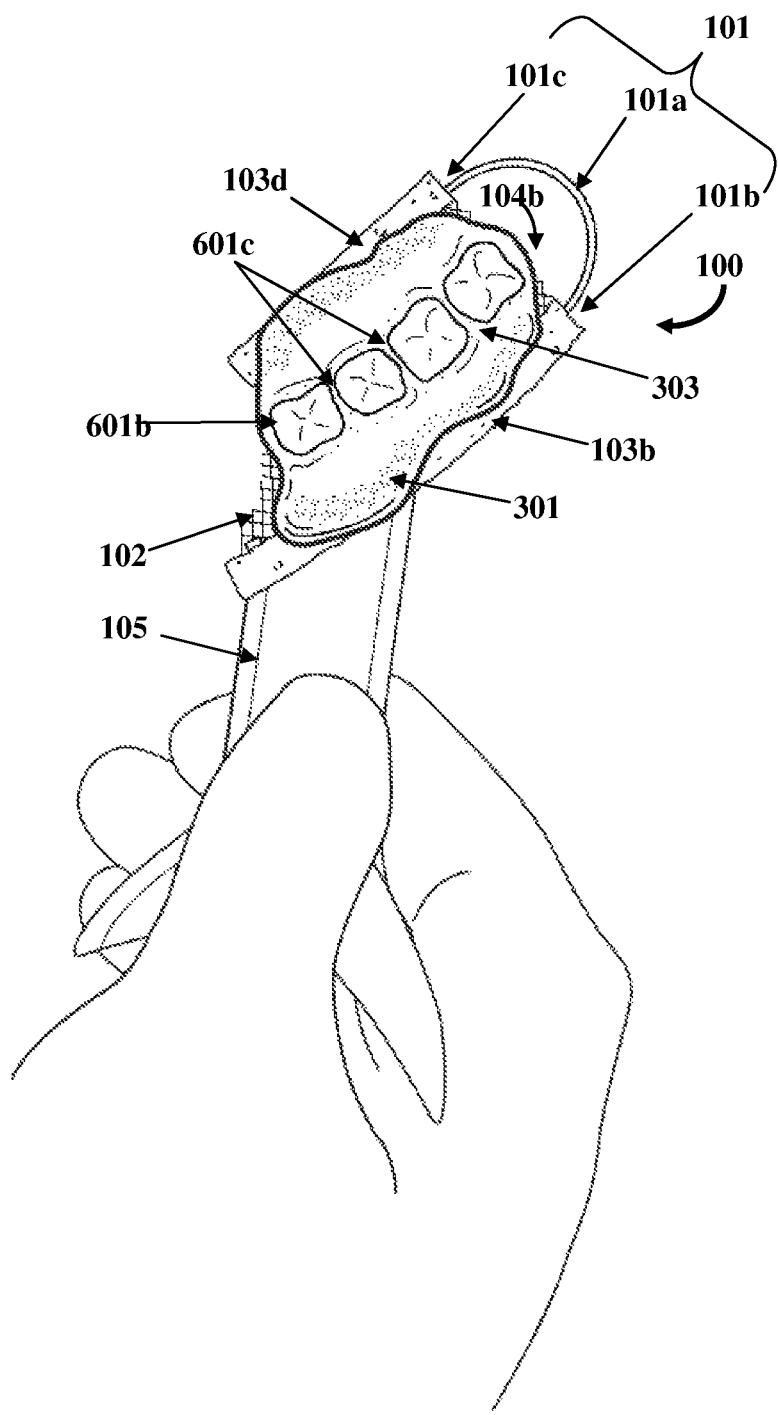
FIG. 6B exemplarily illustrates an orthogonal view of the dental impression apparatus showing a dental impression of the mandibular teeth of the patient.

FIG. 6A and FIG. 6B exemplarily illustrate orthogonal views of the dental impression apparatus 100, showing dental impressions 601a and 601b of the maxillary teeth 305b in the upper trough 104a and the mandibular teeth 305a in the lower trough 104b respectively. The second impression material 303 having a low viscosity shown by sparse shading obtains a finer impression 601a and 601b of the teeth 305b and 305a of the patient, specifically the interstitial spaces 305c between the teeth 305b and 305a when the second impression material 303 is cured. The first impression material 301 having a high viscosity shown by dense shading may obtain a coarser impression 601a and 601b of the teeth 305b and 305a around the second impression material 303, depending on the viscosity of the first impression material 301.

The curing times of both the first impression material 301 and the second impression material 303 ranges, for example, from about 2.5 minutes to about 5 minutes. The second impression material 303, that is, the initial light body material is syringed around the prepared teeth area first, while the first impression material 301, that is, the heavy body impression material is filled in one or both the opposing troughs 104a and 104b defined by the dental impression apparatus 100. Working times may decrease once the dental impression apparatus 100 is placed in the patient's oral cavity. In an embodiment, a medium body impression material is used instead of the heavy and/or light body impression material depending on the preference or needs of the dental practitioner.

Figure 7:
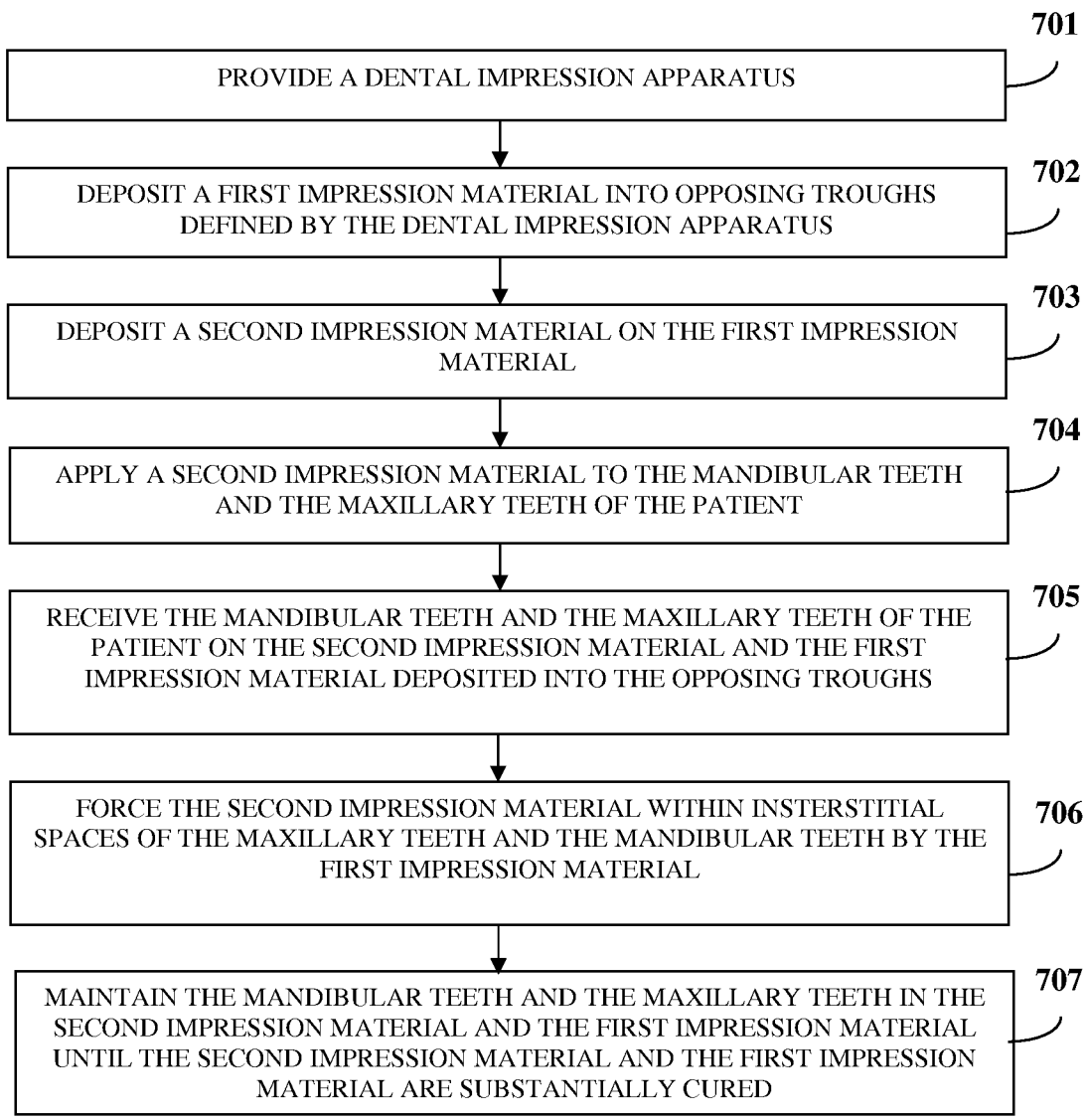
FIG. 7 illustrates a method for obtaining dental impressions of a patient.

FIG. 7 illustrates a method for obtaining dental impressions 601a and 601b of a patient. A dental impression apparatus 100, as disclosed in the detailed description of FIGS. 1A-1B and FIG. 2, is provided 701. The dental impression apparatus 100 disclosed herein comprises the support frame 101 of a predefined shape, the partially permeable membrane 102 mounted on the support frame 101, and the absorbent barrier members 103a, 103b and 103c, 103d mounted to the buccal edge member 101b and the lingual edge member 101c of the support frame 101 to define opposing troughs 104a and 104b separated by the partially permeable membrane 102. The absorbent barrier members 103a, 103b and 103c, 103d absorb moisture, saliva, blood, etc., within the patient's oral cavity. The opposing troughs 104a and 104b are configured to receive the maxillary teeth 305b and the mandibular teeth 305a of the patient respectively. The distal member 101a of the support frame 101 is positioned around one of the patient's posterior molar teeth 306c when obtaining the dental impressions 601a and 601b of the patient.

A first impression material 301 having a high viscosity is deposited 702 into the opposing troughs 104a and 104b defined by the dental impression apparatus 100. A second impression material 303 having a low viscosity is deposited 703 on the first impression material 301. The second impression material 303 may also be applied 704 on the mandibular teeth 305a and the maxillary teeth 305b of the patient. The mandibular teeth 305a and the maxillary teeth 305b of the patient are received 705 on the second impression material 303 and the first impression material 301 deposited into the opposing troughs 104a and 104b. The absorbent barrier members 103a, 103b and 103c, 103d confine a flow of the first impression material 301 and the second impression material 303 within the opposing troughs 104a and 104b, when the patient applies a moderate biting force within the opposing troughs 104a and 104b. The first impression material 301 having a higher viscosity than the second impression material 303 forces 706 the second impression material 303 within the interstitial spaces 305c of the maxillary teeth 305b and the mandibular teeth 305a, as exemplarily illustrated in FIG. 5, to obtain a finer impression 601c of the interstitial spaces 305c of the maxillary teeth 305b and the mandibular teeth 305a. The maxillary teeth 305b and the mandibular teeth 305a are maintained 707 in the second impression material 303 and the first impression material 301 until the second impression material 303 and the first impression material 301 are substantially cured. When the first impression material 301 and the second impression material 303 are cured, the dental impressions 601a and 601b of the maxillary teeth 305b and the mandibular teeth 305a are retained by the first impression material 301 and the second impression material 303 as exemplarily illustrated in FIGS. 6A-6B.

FIGS. 8A-8G exemplarily illustrate a sequence of procedural steps for obtaining dental impressions 601a and 601b of a patient using the dental impression apparatus 100 disclosed herein. With reference to FIGS. 8A-8G, consider an example where the dental impression apparatus 100, as disclosed in the detailed description of FIG. 1A-1B and FIG. 2, is employed for obtaining the dental impressions 601a and 601b of the maxillary teeth 305b and the mandibular teeth 305a of the patient. As exemplarily illustrated in FIG. 8A, the opposing troughs 104a and 104b are configured to receive and conform in shape to the maxillary teeth 305b and the mandibular teeth 305a of the patient respectively, where the upper trough 104a receives the maxillary teeth 305b and the lower trough 104b receives the mandibular teeth 305a. A second impression material 303 having a low viscosity is applied to the mandibular teeth 305a of the patient using the dispensing tube 307 as exemplarily illustrated in FIG. 8B. A first impression material 301 having a substantially higher viscosity that the second impression material 303 is deposited into the opposing troughs 104a and 104b using the dispensing tube 302 as exemplarily illustrated in FIGS. 8C-8D. The second impression material 303 may also be deposited on the first impression material 301 in the opposing troughs 104a and 104b.

Figure 8A:
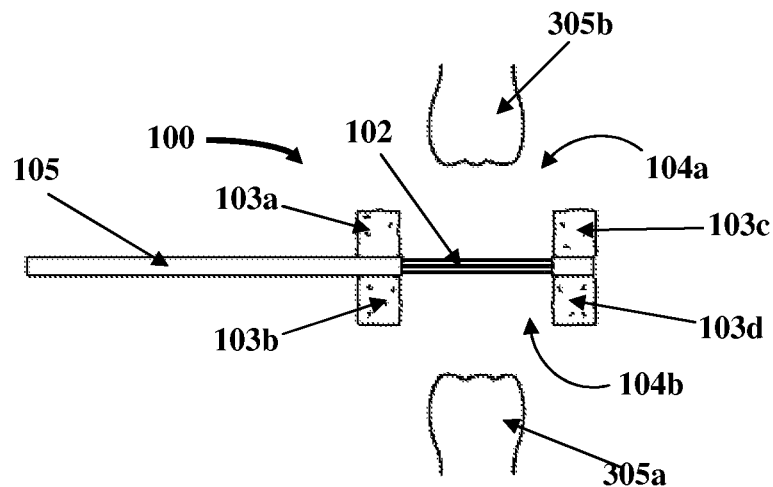
FIG. 8A exemplarily illustrates an upper trough and a lower trough of the dental impression apparatus configured to receive the maxillary teeth and the mandibular teeth respectively.
Figure 8B:
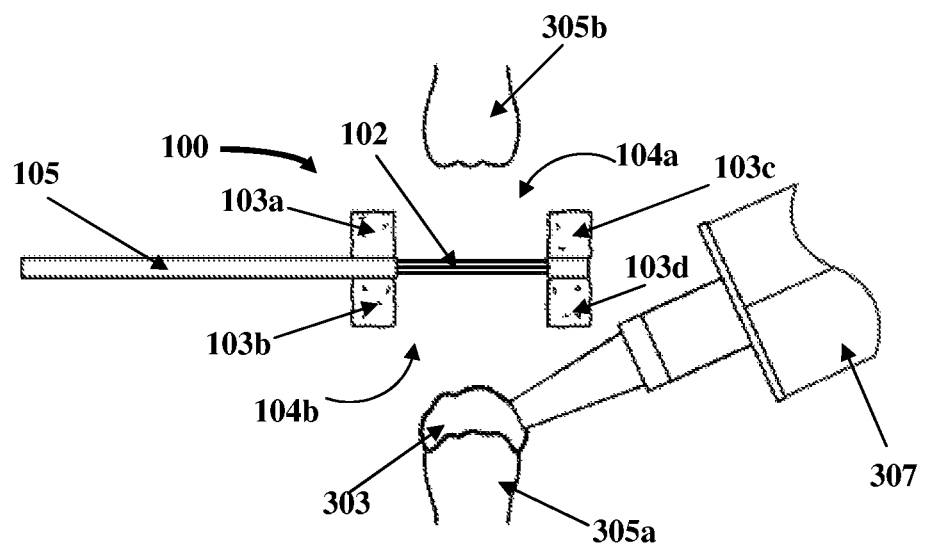
FIG. 8B exemplarily illustrates the application of a second dental impression material to the mandibular teeth using a dispensing tube.
Figure 8C:
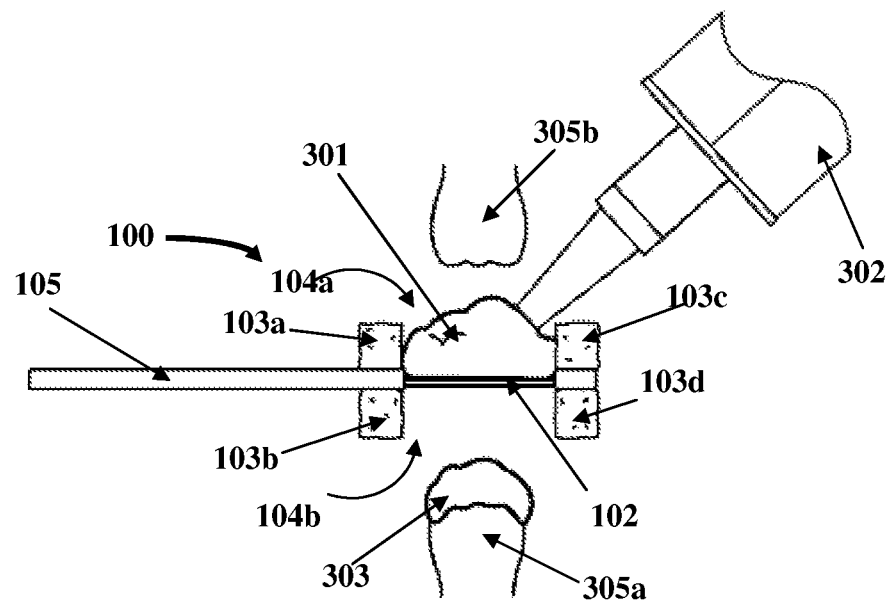
FIG. 8C exemplarily illustrates the application of a first dental impression material on the upper trough of the dental impression apparatus using a dispensing tube.
Figure 8D:
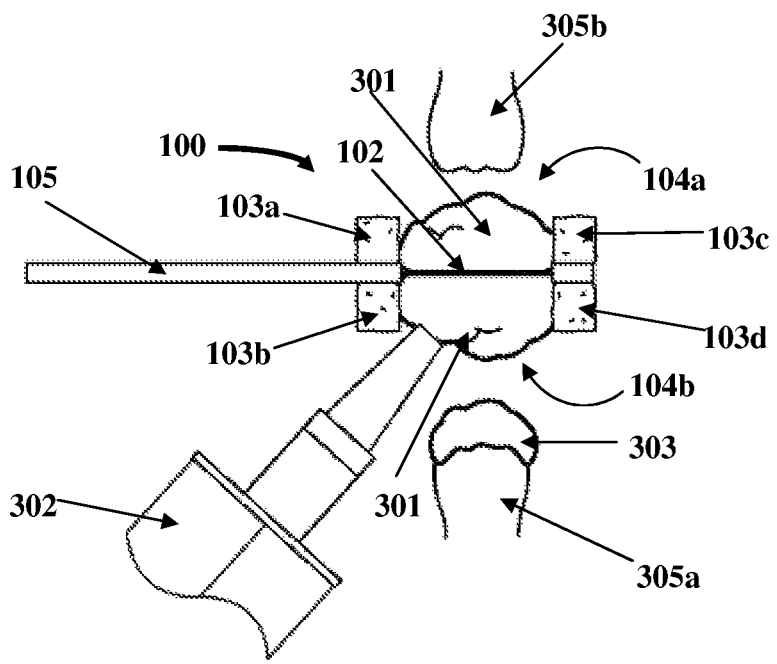
FIG. 8D exemplarily illustrates application of the first dental impression material on the lower trough of the dental impression apparatus using a dispensing tube.
Figure 8E:
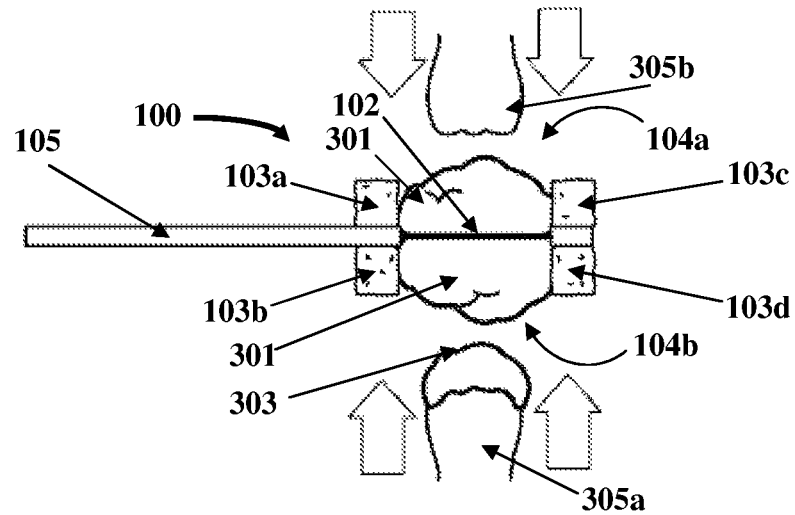
FIG. 8E exemplarily illustrates application of biting force into the upper trough and the lower trough on the dental impression apparatus.
Figure 8F:
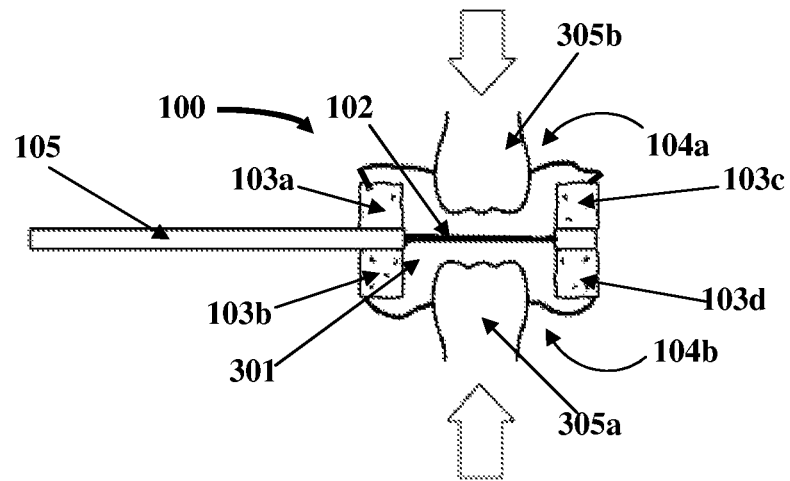
FIG. 8F exemplarily illustrates receipt of maxillary teeth on second impression material and receipt of the mandibular teeth on the first impression material on the dental impression apparatus.
Figure 8G:
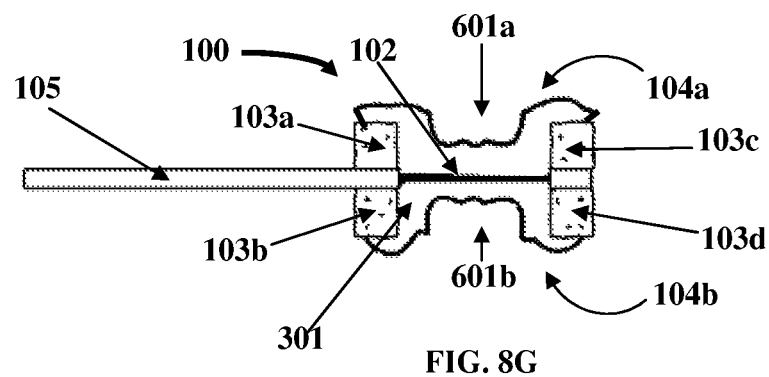
FIG. 8G exemplarily illustrates the dental impression of the maxillary teeth retained on the first impression material and the dental impression of mandibular teeth on the second impression material respectively.

When the patient is instructed to bite into the troughs 104a and 104b by applying a biting force as exemplarily illustrated in FIG. 8E, the patient's maxillary teeth 305b and mandibular teeth 305a are received on the second impression material 303 and the first impression material 301 deposited into the opposing troughs 104a and 104b respectively as illustrated in FIG. 8F. At this step, the absorbent barrier members 103a, 103b and 103c, 103d confine the flow of the first impression material 301 and the second impression material 303 within the opposing troughs 104a and 104b, such that the first impression material 301 having a higher viscosity than the second impression material 303 forces or drives the second impression material 303 deeper into the interstitial spaces 305c of the maxillary teeth 305b and mandibular teeth 305a to obtain high precision dental impressions 601a and 601b.

The patient is instructed to maintain the maxillary teeth 305b and the mandibular teeth 305a in the second impression material 303 and the first impression material 301 until the second impression material 303 and the first impression material 301 are substantially cured. As exemplarily illustrated in FIG. 8F, the absorbent barrier members 103a, 103b and 103c, 103d isolate the teeth 305a and 305b of interest and the impression materials 301 and 303 from the soft tissues, saliva, blood, etc., within the oral cavity of the patient, and prevent contamination of the dental impressions 601a and 601b during the procedure. When the first impression material 301 and the second impression material 303 are cured, the dental impressions 601a and 601b of the maxillary teeth 305b and the mandibular teeth 305a respectively are retained on the first impression material 301 and the second impression material 303 as exemplarily illustrated in FIG. 8G.

The first dental impression material and said second dental impression material are configured to simultaneously capture a dental impression of the maxilliary teeth, the mandibular teeth and a centric occlusion of the maxillary teeth and the mandibular teeth when a biting force is applied by said patient into said first and second troughs.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

We claim:

1. A dental impression apparatus for obtaining a dental impression and a bite registration of maxillary and mandibular teeth, comprising:
   a lingual edge member comprising a top surface, a bottom surface and an inner edge;
   a buccal edge member comprising a top surface, a bottom surface and an inner edge;
   a distal member, said buccal edge member and said lingual edge members being elongated and generally parallel and extending from the opposing ends of said distal member, said distal, lingual and buccal members in combination defining a support frame, said support frame conforming to a dental arch of a patient;
   a handle extending obliquely from said buccal edge member;
   a partially permeable membrane, said partially permeable membrane extending from said inner edge of said buccal edge member to said inner edge of said lingual edge member;
   a first trough defined by said partially permeable membrane, a first absorbent barrier member and a second absorbent barrier member, wherein said partially permeable membrane defines a base of said first trough, wherein said first absorbent barrier member defines a first wall of said first trough, and wherein said second absorbent barrier member defines a second wall opposite to said first wall of said first trough;
   a second trough disposed below said first trough, said second trough defined by said partially permeable membrane, a third absorbent barrier member and a fourth absorbent barrier member, wherein said partially permeable membrane defines said base of said second trough, wherein said third absorbent barrier member defines a first wall of said second trough, wherein said fourth absorbent barrier member defines a second wall opposite to said first wall of said second trough;
   said first and third absorbent barrier members extend from a top side and a bottom side of said buccal edge member along an entire length of said buccal edge member;
   said second and fourth absorbent barrier members extend from a top side and a bottom side of said lingual edge member along an entire length of said lingual edge member;
   wherein said first trough is configured to receive one or more of the maxillary teeth of a patient and said second trough is configured to simultaneously receive one or more of the mandibular teeth of said patient;
   wherein all of said first wall and said second wall of said first trough are absorbent and all of said first wall and said second wall of said second trough are absorbent;
   wherein said support frame is composed of metal alloy, stainless steel or high density polyethylene.

2. The dental impression apparatus of claim 1, wherein said partially permeable membrane comprises one of a cotton fabric, a nylon mesh, and a polyethylene screen.

3. The dental impression apparatus of claim 1, wherein each of said first, second, third and fourth absorbent barrier members is composed of a one of a low density polyethylene foam, a cotton sponge, and a cotton polyethylene blend.

4. A method for obtaining a dental impression of maxillary and mandibular teeth of a patient, comprising:
   providing a dental impression tray comprising:
      a lingual edge member comprising a top surface, a bottom surface and an inner edge;
      a buccal edge member comprising a top surface, a bottom surface and an inner edge;
      a distal member, said buccal edge member and said lingual edge member being generally parallel and extending from the opposing ends of said distal member, said distal, lingual and buccal members in combination defining a support frame, said support frame conforming to a dental arch of a patient;
      a handle extending obliquely from said buccal edge member;
      a partially permeable membrane, said partially permeable membrane extending from said inner edge of buccal edge member to said inner edge of lingual edge member;
   a first trough defined by said partially permeable membrane, a first absorbent barrier member and a second absorbent barrier member, wherein said partially permeable membrane defines a base of said first trough, wherein said first absorbent barrier member defines a first wall of said first trough, and wherein said second absorbent barrier member defines a second wall opposite to said first wall of said first trough;
   a second trough disposed below said first trough, said second trough defined by said partially permeable membrane, a third absorbent barrier member and a fourth absorbent barrier member, wherein said partially permeable membrane defines said base of said second trough, wherein said third absorbent barrier member defines a first wall of said second trough, wherein said fourth absorbent barrier member defines a second wall opposite to said first wall of said second trough;

said first and third absorbent barrier members extend from a top side and a bottom side of said buccal edge member along an entire length of said buccal edge member;

said second and fourth absorbent barrier members extend from a top side and a bottom side of said lingual edge member along an entire length of said lingual edge member;

wherein said first trough is configured to receive one or more of the maxillary teeth of a patient and said second trough is configured to simultaneously receive one roe more of the mandibular teeth of said patient;

wherein all of said first wall and said second wall of said first trough are absorbent and all of said first wall and said second wall of said second trough are absorbent;

wherein said support frame is composed of metal alloy, stainless steel or high density polyethylene.

placing a dental impression material into said upper and said lower troughs;

receiving a biting force from the teeth of a patient in said first trough and said second trough;

curing said dental impression material.

* * * * *